United States Patent [19]
Melling

[11] Patent Number: 5,754,722
[45] Date of Patent: May 19, 1998

[54] FIBER-OPTIC SPECTROSCOPIC PROBE WITH INTERCHANGEABLE SAMPLING HEADS

[76] Inventor: Peter J. Melling, 512 Leadmine Rd., Sturbridge, Mass. 01566

[21] Appl. No.: 380,078

[22] Filed: Jan. 30, 1995

[51] Int. Cl.[6] .................................................. G02B 6/04
[52] U.S. Cl. ....................... 385/115; 385/117; 385/120; 356/436; 250/576
[58] Field of Search ................................ 385/115–120; 356/440, 436; 250/576; 362/105

[56] References Cited

U.S. PATENT DOCUMENTS

| | | | |
|---|---|---|---|
| 4,234,910 | 11/1980 | Price | 362/105 |
| 4,955,687 | 9/1990 | Pafford | 385/116 |
| 5,381,237 | 1/1995 | Sela | 356/436 |
| 5,412,749 | 5/1995 | Sayegh et al. | 385/115 |

*Primary Examiner*—Phan T. H. Palmer

[57] ABSTRACT

A fiber-optic spectroscopic probe for use with a Fourier Transform Infrared (FTIR) spectrometer for sensing the absorption of infrared energy by a sample has a shaft containing a fiber optic bundle which terminates proximate the end of the shaft for transmitting and receiving infrared energy from the sample being measured by a measuring head. The shaft has means for detachably attaching interchangeable measuring heads for measuring attenuated total reflectance, diffuse or specular reflectance of the sample, or for measuring the infrared energy transmitted through the sample. The interchangeable heads are coupled to the shaft without the use of additional optics or mechanical positioning devices. The shaft assembly may include a cooling jacket for measuring samples at elevated temperatures. Having different, interchangeable spectral sampling heads makes it possible to obtain quantitative spectral data from a wide range of samples in varying states of agglomeration and homogeneity using a single device.

6 Claims, 16 Drawing Sheets

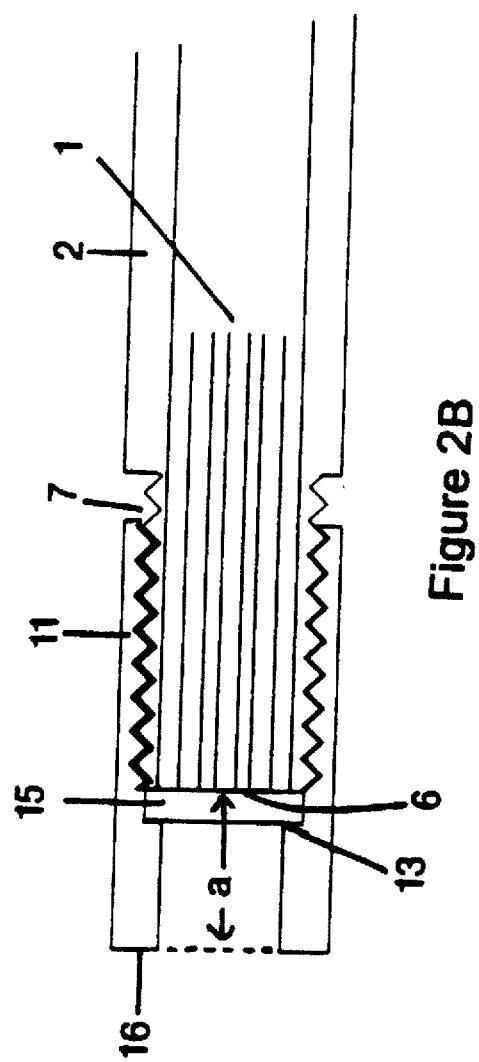

FIBER-OPTIC SPECTROSCOPIC PROBE WITH INTERCHANGEABLE SAMPLING HEADS

BACKGROUND OF THE INVENTION

1. Field of the Invention

The present invention relates to accessories used in conjunction with spectrophotometers and spectrometers, more particularly with Fourier Transform Infrared (FTIR) spectrometers. These accessories utilize infrared-transmitting optical fibers to enable spectral analysis of samples remote from the body of the FTIR spectrometer using recognized sampling means such as attenuated total reflectance (ATR), diffuse reflectance, and transmission.

2. Prior Art

The use of ATR crystals and transmission cells remotely linked to FTIR spectrometers by way of fiber optics is well known. Single-fiber systems (systems using one input and one output optical fiber) are commonly used and generally include complex coupling means to transfer IR radiation from the optical fiber into the ATR crystal or transmission cell and back again. For example, U.S. Pat. No. 5,185,834 (to Day and Poulter, assigned to Specac Ltd.) describes complex mechanical means for positioning the fibers and focusing the energy from the sample onto the very small target provided by the end of a single return optical fiber. Fiber-optic accessories for remote spectroscopy using the method of diffuse reflectance are also known. For example, U.S. Pat. No. 5,166,756 (to McGee and Von Bargen, assigned to NIR Systems) describes a means for minimizing interference by specular reflectance in a diffuse-reflectance fiber-optic probe for near IR spectroscopy of powders; specular reflectance can present a particular problem in systems operating in the near IR using silica-based optical fibers which typically have a relatively low numerical aperture (NA).

SUMMARY OF THE INVENTION

It is an object of the present invention to provide a convenient means for obtaining mid-IR spectra from samples in a variety of physical forms and states, using an assembly which comprises an optical fiber cable to transfer the signal from a IR light source to the sample, and from the sample to an IR detector; the light may be modulated either at the source or at the detector. The chemical signature may be obtained from the sample by means of ATR, transmission, or diffuse and specular reflectance, using interchangeable ATR, transmission and reflectance sample-measuring heads which can be coupled to the fiber-optic cable without the use of additional optics or mechanical positioning devices.

In the case of ATR, the ATR element is coupled to the fiber cable by directly butting the ends of the optical fibers against the end of the ATR crystal (as described in U.S. Pat. No. 5,170,056 to Berard, Burger, Melling, and Moser, assigned to Galileo Electro-Optics). When fiber materials of relatively high numerical aperture NA, such as mid-IR-transmissive chalcogenide glasses are used, and when the fibers are bundled, IR radiation can be efficiently transferred between the optical fibers and the crystal without focusing. The ATR method was developed for use with strongly absorbing or scattering liquids in which a short path length through the sample is necessary. ATR is the preferred method for obtaining spectra from liquid samples having a high molar extinction coefficient; in favorable circumstances, spectra can be obtained from aqueous solutions using ATR. The method also works well for pastes and viscous mixtures, and can be used to obtain spectra in liquids containing suspended solids (for example, the catalyst in a heterogeneously catalyzed chemical reaction) or in which effervescence is present.

The transmission cell is provided with a screw fitting which allows it to be directly substituted for the ATR head at the end of the fiber-optic cable. Transmission mode is suitable for obtaining spectra in cases where the analyte is too weakly absorbing for effective use of ATR. The absorbence characteristics of IR samples depend on both the concentration and the molar extinction coefficient of the IR-active species. A device having both ATR and transmission capabilities can be used over a wider concentration range and for a greater variety of chemical species than a device having only ATR or only transmission mode available.

For diffuse/specular reflectance, the end of the fiber cable may optionally be protected by an IR-transmitting window. Reflectance methods are suitable for obtaining spectra from solids, powders, thin films, and coatings or corrosion layers. In the case of powders, for instance, the reflection mode is predominantly diffuse; a specular reflectance component may be present but in most cases, a predominantly diffuse reflectance spectrum can be readily obtained.

A single optical fiber cable is provided with interchangeable parts so that all three methods of obtaining the spectrum (ATR, transmission, and reflectance) are conveniently available. It is a particular object of the invention to provide a fiber-optic spectroscopic probe which can be conveniently changed from ATR to reflectance to transmission mode by simply changing a screw-fitted head at the end of the probe.

It is a further object of the invention to optimize capture of the signal from the sample for transmission back to the detector. Effective coupling of the sample signal into the receiving fibers depends among other things on the numerical aperture (NA) of the particular optical fibers that are used. Various arrangements of transmitting and receiving fibers are possible within the cable. In all cases, optical fibers having a relatively high NA are preferred, so as to maximize the capture of light from the sample. By providing interchangeable spectral sampling cells or attachments, each of which is designed to take the fullest advantage of the optical characteristics of the fiber optics, it is possible to obtain useful, quantitative spectral data from a wide range of samples in varying states of agglomeration and homogeneity.

BRIEF DESCRIPTION OF THE DRAWINGS

FIG. 2B is a sectional view of a double pass reflectance attachment for the fiber-optic probe

Figure 1:
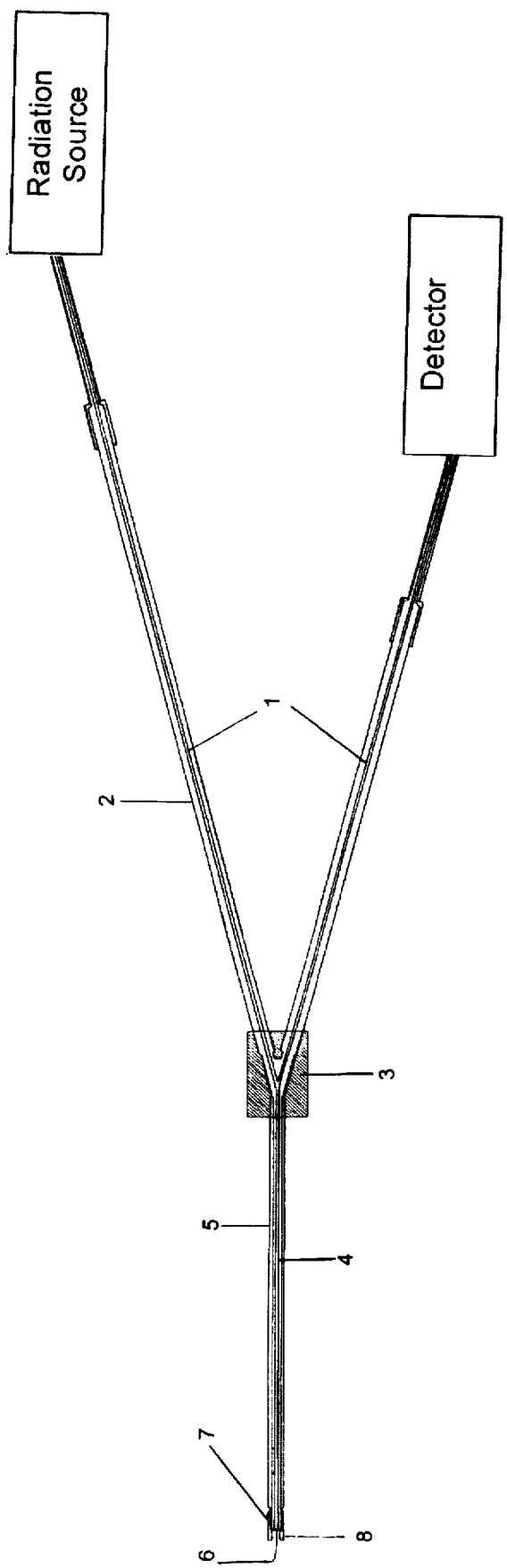
FIG. 1 is an illustration of a probe with fiber-optic bundles

| Reference Numerals in Drawings | |
|---|---|
| 1 Optical fiber bundle | 2 Flexible casing |
| 3 Splitter | 4 Combined optical fiber bundle |
| 5 Shaft | 6 Flat bundle end |
| 7 Screw thread | 8 Interchangeable screw-threaded head |
| 9 Input light | 10 Output light |
| 11 Screw-threaded head | 12 Ferrule |
| 13 Retaining notch | 14 ATR crystal |
| 15 Protective window | 16 Flat end |
| 17 Spacer | 18 Inlet holes |
| 19 Threaded end plug | 20 Reflective surface |
| 21 Optical fiber delivering light from | 22 Illuminated area of sample surface |
| 23 Optical fiber returning light to | 24 Cooling jacket |
| 25 Inner tube | 26 Outer tube |
| 27 Water inlet | 28 Water outlet |
| 29 Threaded compression fitting | 30 Threaded compression fitting |
| 31 Securing ring | 32 O-ring |
| 33 ATR crystal guard | 34 Slits |

DETAILED DESCRIPTION OF THE PREFERRED EMBODIMENTS

A sketch of a preferred embodiment of the probe with fiber-optic bundles is shown in FIG. 1. The probe consists of fiber-optic bundles (1) with flexible casings (2) which are joined at a splitter (3) where the two bundles are combined into one (4) and formed into a shaft with a rigid casing (5) and a flat, optically polished end (6). The end of the shaft casing is provided with a screw thread (7) for the attachment of an interchangeable screw-threaded head (8). Light from a light source enters the probe (9), travels along the input fibers, through the splitter and shaft, and into the sample by way of the selected sample-measuring head. The light from the sample is collected by the return fibers at the shaft end and is transmitted through the return fibers in the shaft, the splitter, and the flexible bundle to leave the probe (10) and travel to a detector. In the preferred case, the light is in the IR region of the EM spectrum and the optical fibers are made from an IR-transmitting material such as chalcogenide glass, fluoride glass, polycrystalline silver halide, etc. The shaft and the interchangeable heads are typically made from stainless steel, although other materials such as Hastelloy (TM) or (optionally filled) Teflon (TM) may be used in corrosive or hot environments.

Figure 2A:
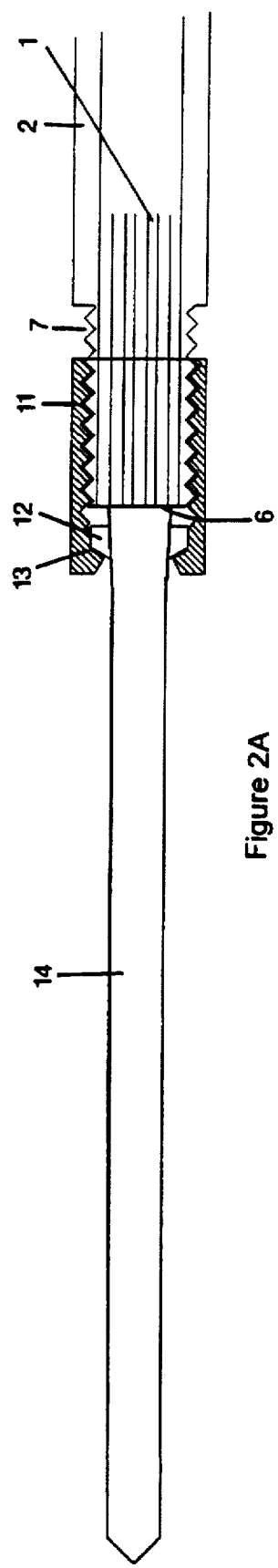
FIG. 2A is a sectional view of an ATR attachment for the fiber-optic probe

FIG. 2A shows a cross-section of a preferred design for the ATR Head. An ATR crystal (14) is held in position against the flat end of the fiber bundle by a screw-threaded head (11) which is provided with a retaining notch that supports a ferrule (12) gripping the ATR crystal. This direct "butt-coupling" of the ATR crystal to the end of the fiber bundle is the preferred coupling method. However, the design will also accommodate an intermediate or relay optic between the crystal and the fiber bundle if environmental factors such as thermal conduction make this necessary. Zinc selenide is the preferred material for the ATR crystal; zinc sulfide may also be used, or any other light-transmissive material such as germanium, silver halide, silicon, KRS-5, IR-transmissive glasses and polymers may also be used if they offer suitable mechanical strength and chemical resistance. The ATR crystal may be coated with a thin layer of IR-transmissive material such as diamond, or diamond-like carbon, to provide enhanced chemical resistance. It may also be optionally coated with a chemically reactive layer such as an enzyme or a polymer or other material that reversibly concentrates the analyte from the sample solution.

A preferred design for the Reflectance Head is shown in cross-section in FIG. 2B. The screw-threaded head (11) is provided with a retaining notch (13) for an optional protective window (15) made from an appropriate light-transmissive material. The end of the probe head (16) is flat; this end is in direct contact with the sample during collection of spectra. The end of the head extends by the distance a beyond the end of the fiber-optic bundle, forming a "collar" which prevents the lateral escape of reflected light. The value of $\alpha$ is determined empirically to maximize total reflected power.

Figure 2C:
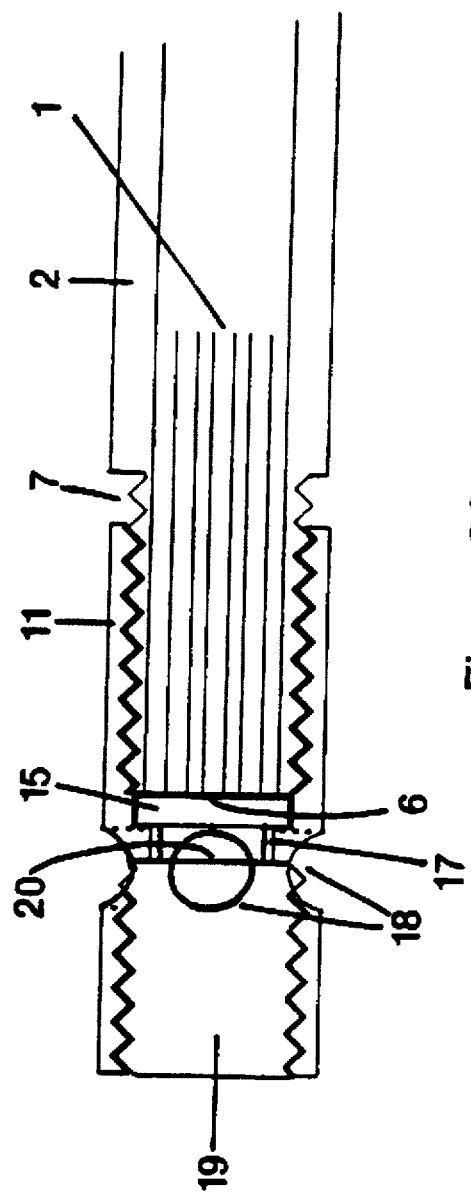
FIG. 2C is a sectional view of a transmission attachment for the fiber-optic probe
Figure 2D:
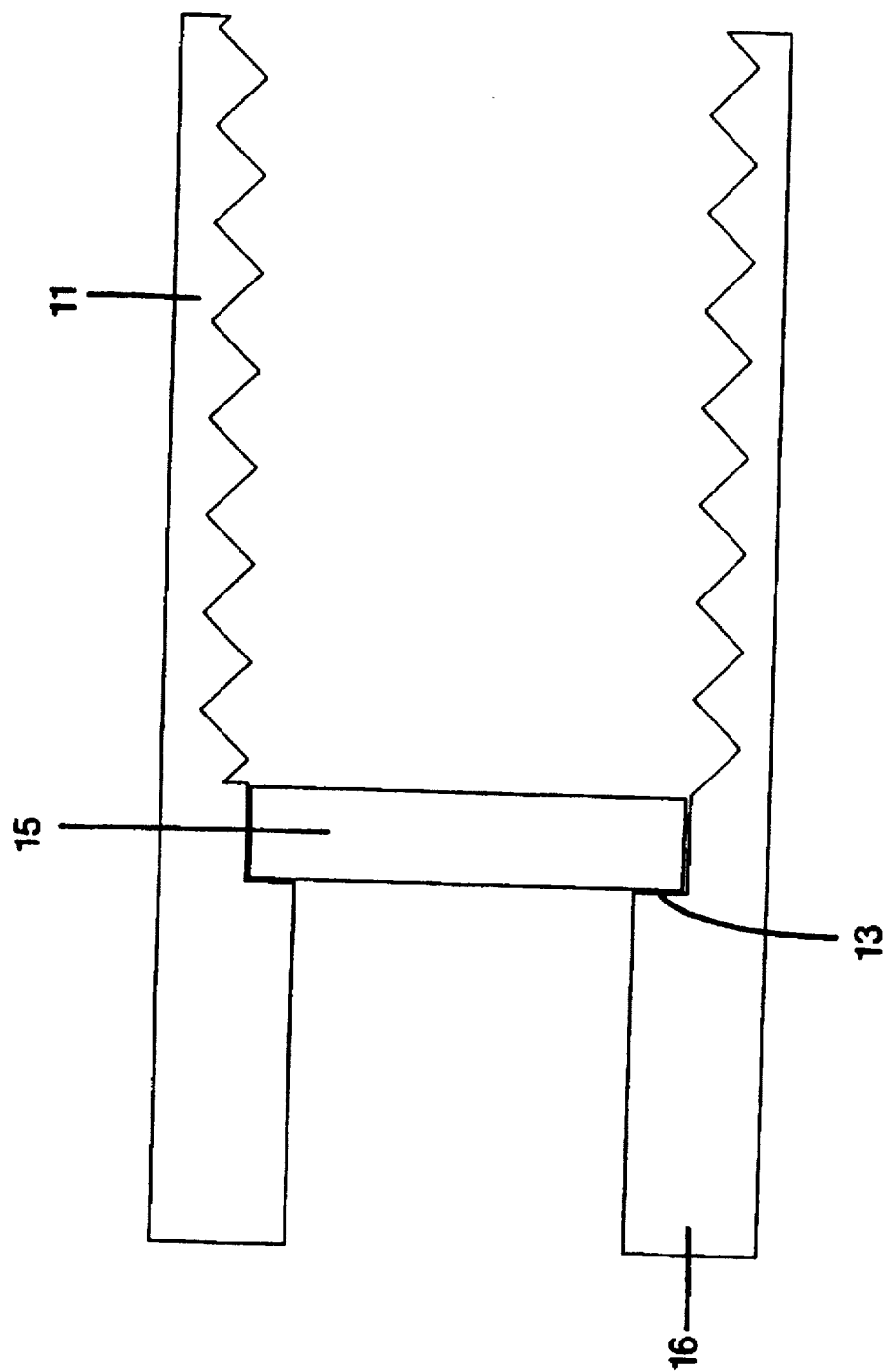
FIG. 2D is a sectional view of a reflectance attachment
Figure 2E:
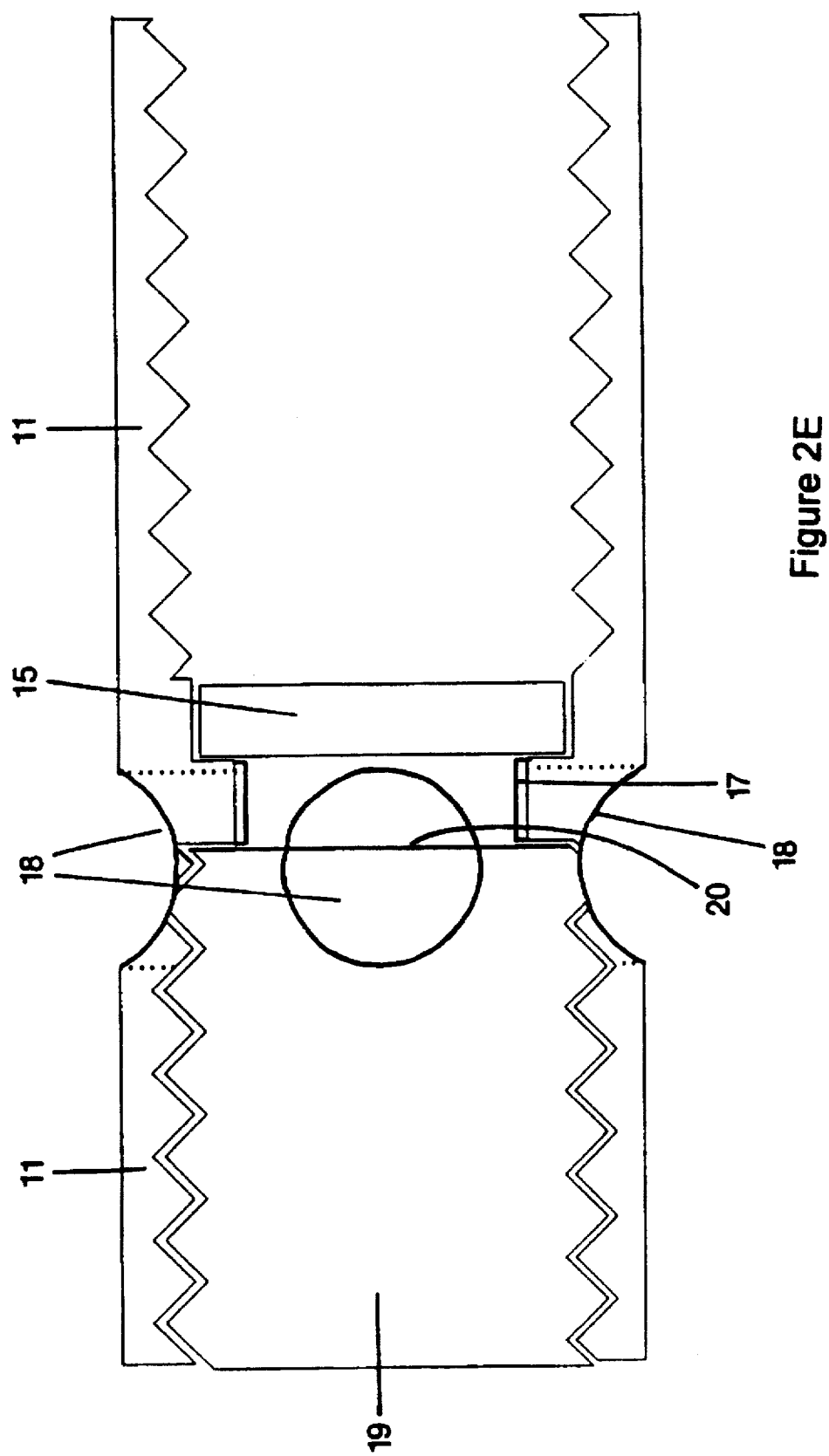
FIG. 2E is a sectional view of a double-pass transmission attachment

FIG. 2C shows a preferred design for the Transmission Head in cross-section. The screw-threaded head (11) is provided with a retaining notch (13) for the optional protective window (15) and with inlet holes (18) to allow ingress of the liquid or gaseous sample while minimizing the formation and retention of bubbles. A spacer (17) is positioned next to the window; the size of the spacer determines the path length of the transmission cell. The threaded end plug (19) has a reflective surface (20) to return the input light back through the sample to the fiber-optic bundle. This surface may optionally be curved to direct the maximum return of light to the central fibers in the bundle, which are return fibers in the most preferred design. In addition, curvature of the reflective surface improves the capture of divergent light. In use, the input radiation passes from the fiber-optic bundle through the sample contained in the cell (1st pass) and is reflected from surface (20) back through the sample (2nd pass) to the end of the fiber-optic bundle to give an overall path length equal to double the internal length of the cell.

Figure 3:
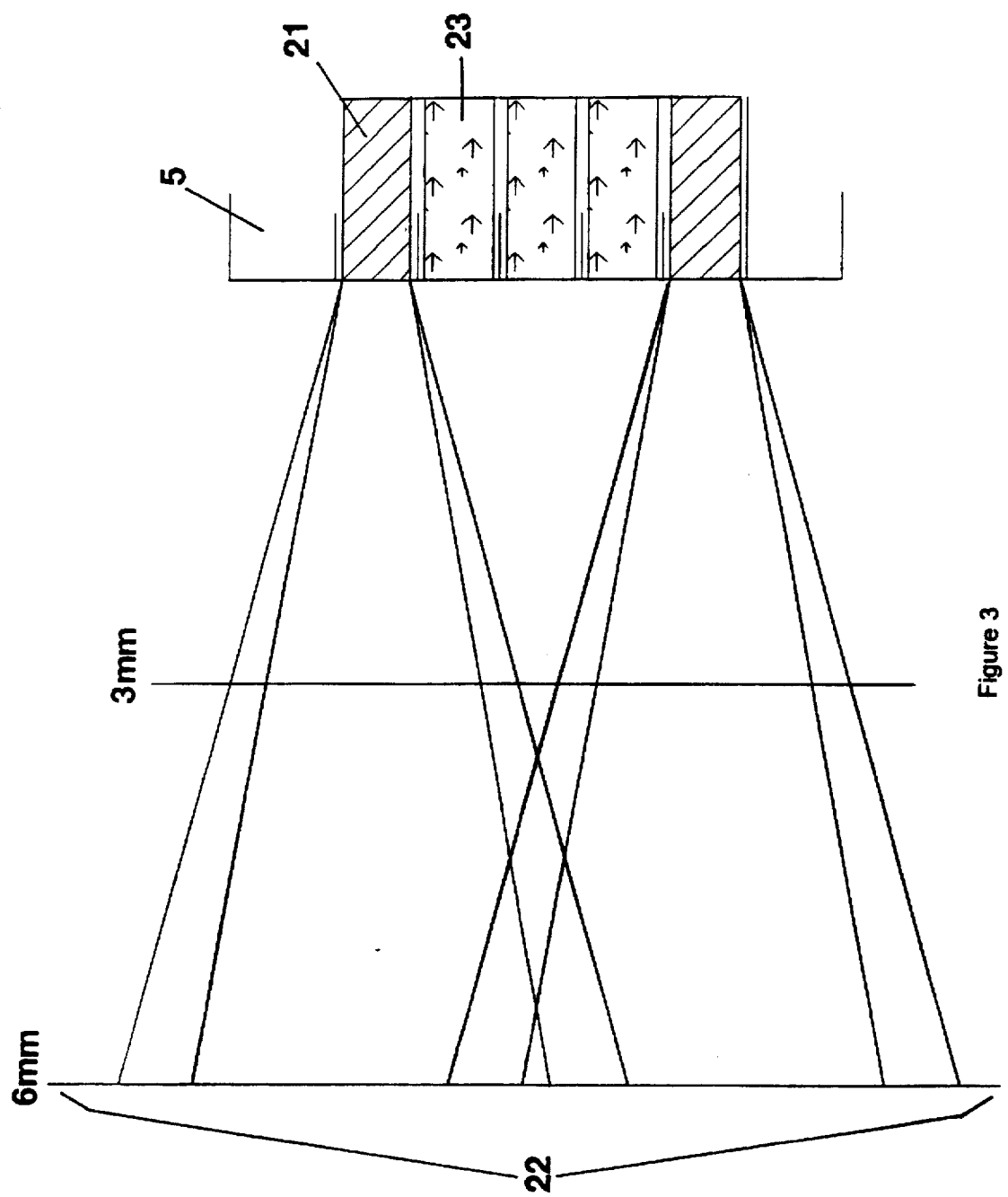
FIG. 3 is a ray diagram illustrating the operation of the reflectance attachment
Figure 4:
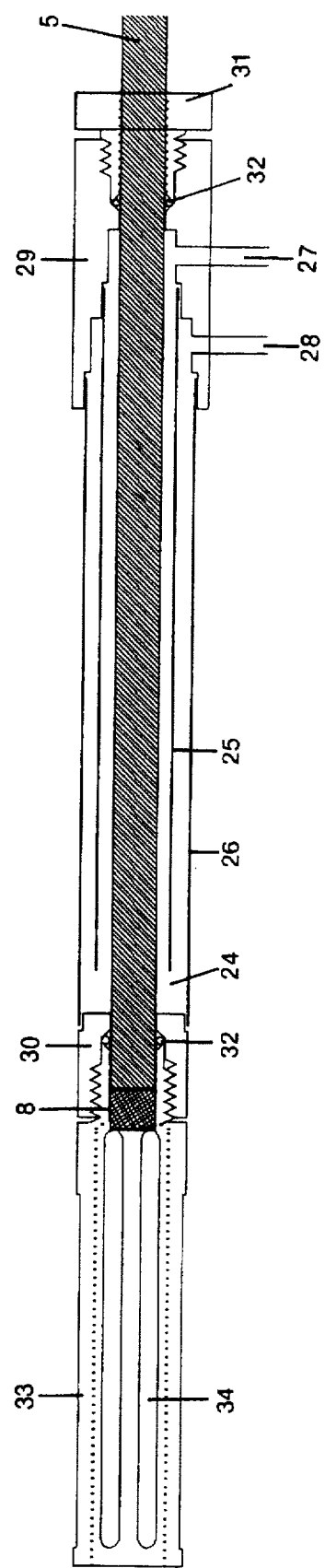
FIG. 4 is a sectional view of a cooling jacket combined with an optional guard for the ATR crystal

The arrangement of fibers in the combined bundle which forms the probe shaft may be random, or the input and return fibers may be arranged in any desired configuration. The light returning from the sample bathes the entire end of the fiber-optic bundle; it is therefore advantageous to have more return fibers than input fibers, so as to maximize the fraction of the bundle that returns light to the detector and thus maximize the signal delivered to the detector. In one preferred embodiment, there are twelve return fibers and seven input fibers. FIG. 3 illustrates (for the case of diffuse reflectance) the illumination area that is achieved using one of the preferred configurations of fibers within the combined bundle of return and input fibers. The wide illumination area (22) in FIG. 3 is calculated based on fibers having NA of 0.3; typical glass-clad chalcogenide glass fibers have NA even higher than this. The input fibers (21) are arranged around the periphery of the bundle, with return fibers (23) in the center, a configuration which has been shown by computer modeling to be advantageous for operation in ATR mode. With such a wide illumination area, diffusely scattered light from the sample bathes the return fibers, leading to unexpectedly good performance of the diffuse reflectance head when high-NA fibers are used in the illustrated configuration. An additional feature which can be included in the fiber-optic probe system is the cooling assembly illustrated in FIG. 4. A cooling jacket (24), comprising two concentric tubes (25 and 26) of a size to fit around the shaft (5) of the fiber-optic probe, is provided with threaded compression-fittings (29 and 30) which are welded or soldered to the jacket. The fitting distant from the sampling head (27) is provided with a water inlet (27) which feeds cooling water into the inner tube (25) of the jacket and a water outlet (28) which removes water from the outer tube. Both compression fittings are further provided with O-rings (32) which are compressed in use to give a tight fit against the shaft casing. The fittings are secured in use by securing rings (31). When the ATR sampling head is in use, the fitting adjacent to the head may optionally be secured with a ring which comprises a guard (33) for the protection of the ATR crystal. The guard is in the form of cylinder provided with slits (34) for the ingress of fluid sample. When other sampling heads are in use, a securing ring (not shown) similar to that at the distal end of the cooling attachment may be used. The use of this cooling jacket enables the use of the fiber-optic probe in environments heated to at least 200 deg. C. without damage to the fiber-optic assembly or significant degradation of the observed spectrum. The range of operation of the probe is thus extended even further.

The following examples illustrate the operation of the fiber-optic probe with each of the three sampling heads that have been described:

EXAMPLE 1

ATR Head

Figure 5A:
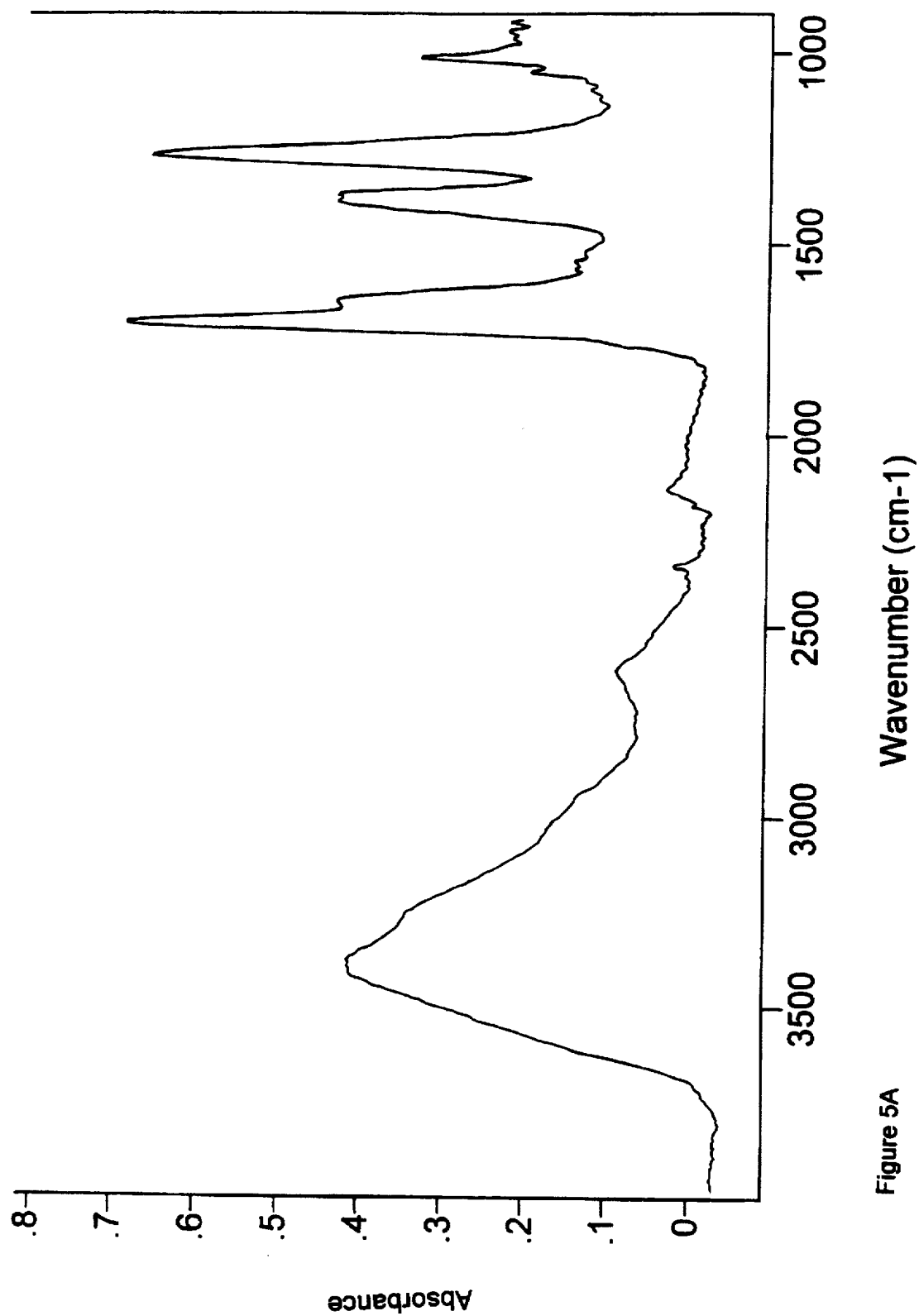
FIG. 5A is an FTIR spectrum of a 50/50 wt. % aqueous solution of acetic acid, referenced to air
Figure 5B:
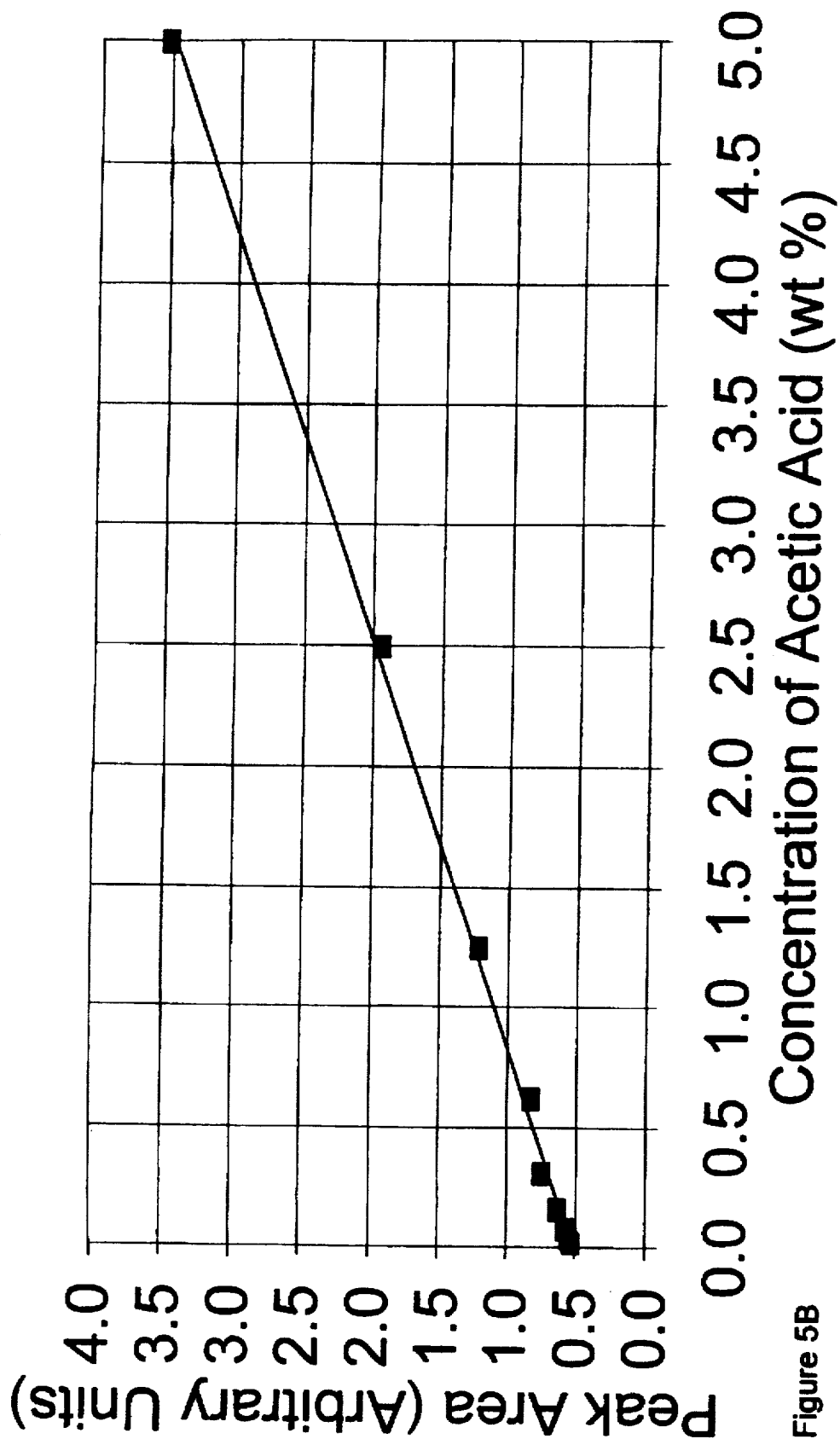
FIG. 5B is a calibration plot of the concentration of acetic acid in water based on FTIR spectra (referenced to a water background for calibration)

FIG. 5A shows the FTIR spectrum of aqueous acetic acid, obtained by attaching the ATR head to an IR fiber-optic probe and dipping it into a sample of 50 wt. % acetic acid in water. The spectrum was acquired for approx. 2 minutes using a typical commercial FTIR spectrometer (from Midac Corporation) and was referenced against air. FIG. 5B shows a calibration plot obtained by mixing known quantities of acetic acid and water to give a series of solutions with concentrations in the range 0–5 wt. % acetic acid. The FTIR spectra were obtained as in the previous case, with the exception that water was used as the reference. The calibration plot is based on the calculated area of the acetic acid peak at 1710 $cm^{-1}$, and shows a good linear response even at concentrations below 0.2 wt. % acetic acid.

EXAMPLE 2

Reflectance Head

Figure 6A:
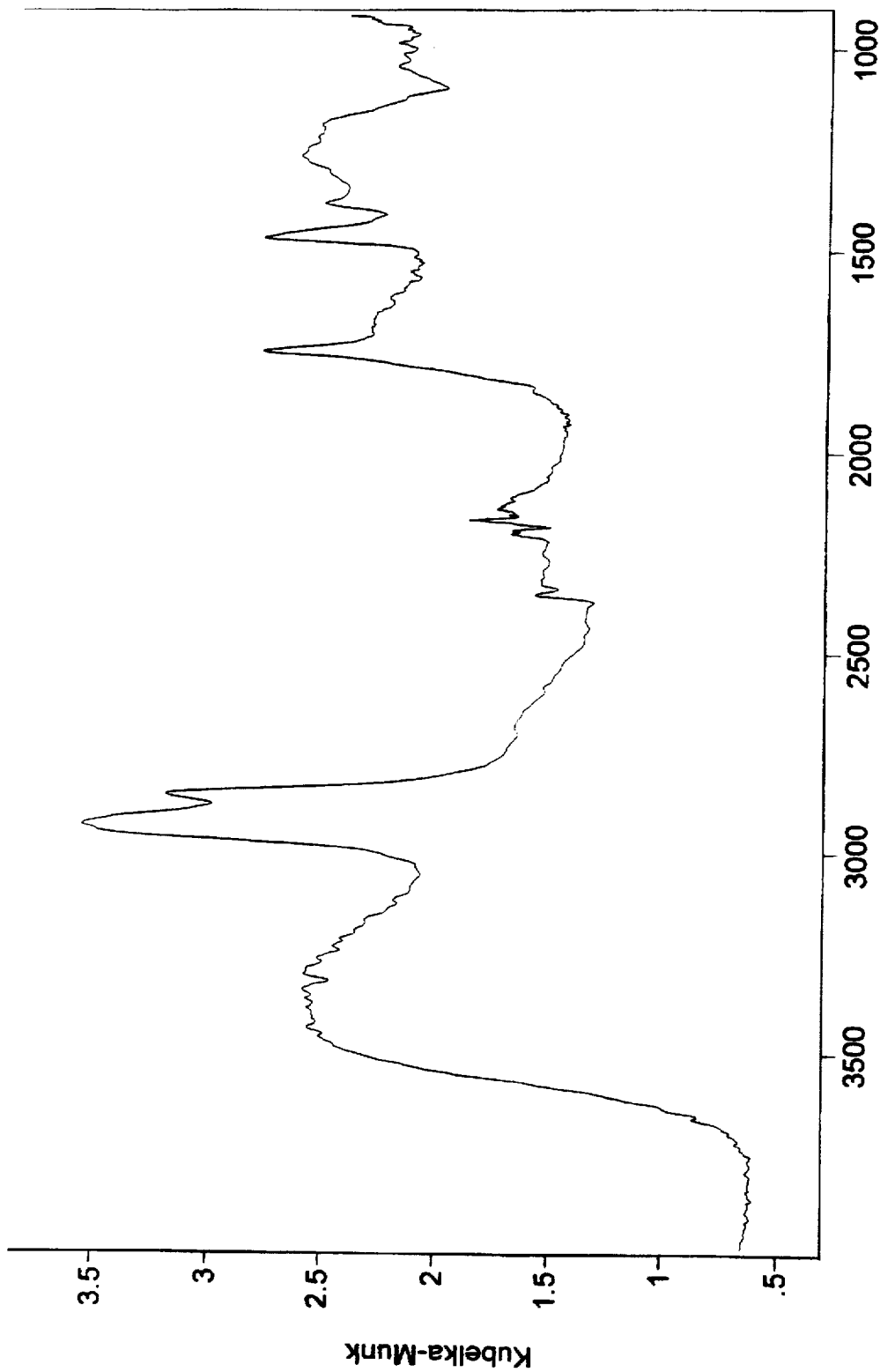
FIG. 6A is an FTIR spectrum of a surface painted with vermilion pigment in linseed oil
Figure 6B:
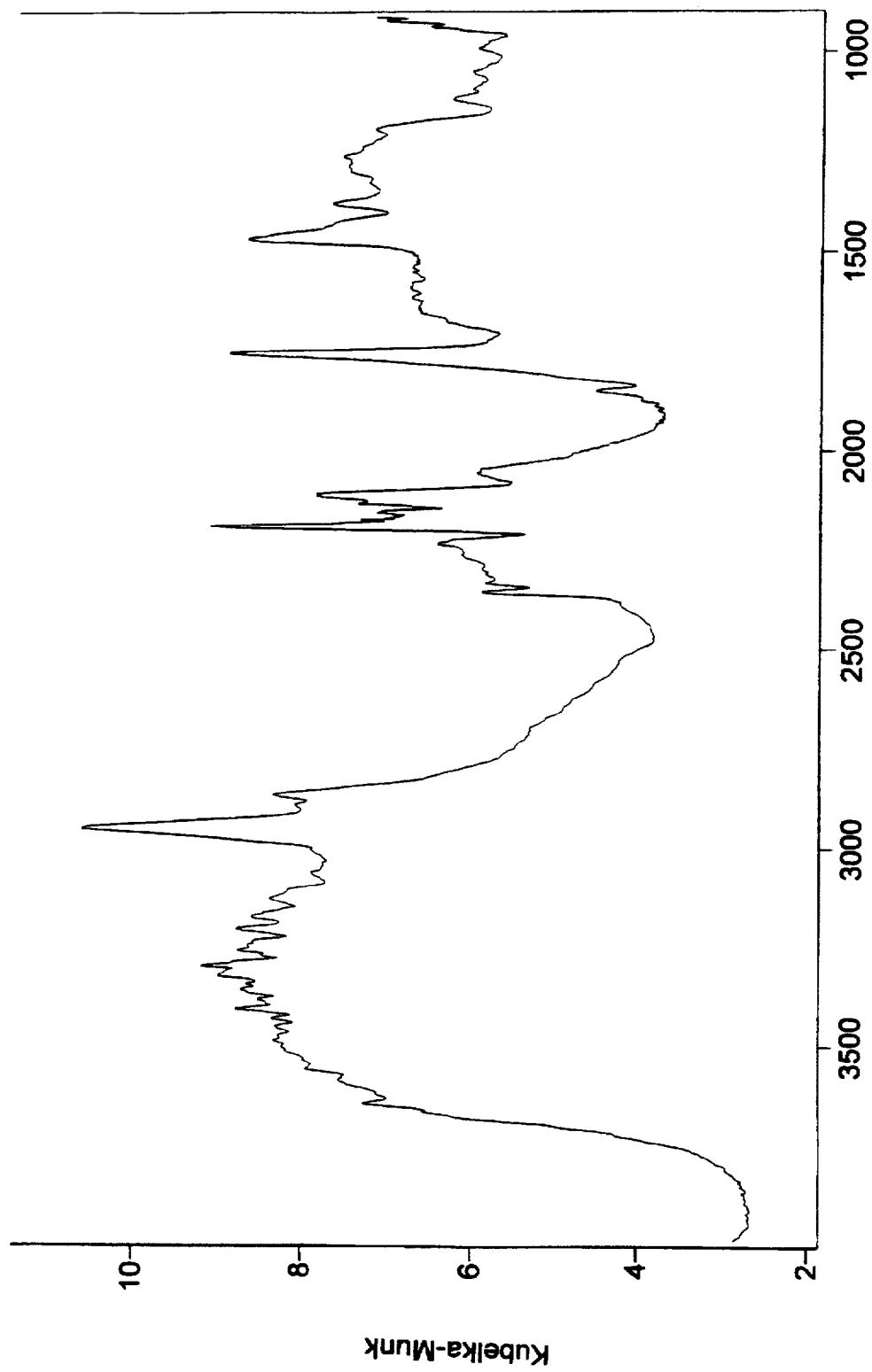
FIG. 6B is an FTIR spectrum of a surface painted with Prussian blue pigment in linseed oil

FIGS. 6A and 6B show the FTIR spectra of pigments (vermilion and Prussian blue, respectively) suspended in linseed oil and applied as paints over wood. To obtain the spectra, the reflectance head was attached to the probe and the flat end of the head was placed against the surface of each paint. In the particular reflectance head used for this experiment, the end of the fiber bundle was supported 4 mm above the sample surface when the head was in position. The spectra were acquired for approx. 2 minutes each, and differences are clearly observable. This method can be used to characterize quite small areas of paint in a convenient and completely nondestructive fashion.

EXAMPLE 3

Reflectance Head

Figure 6C:
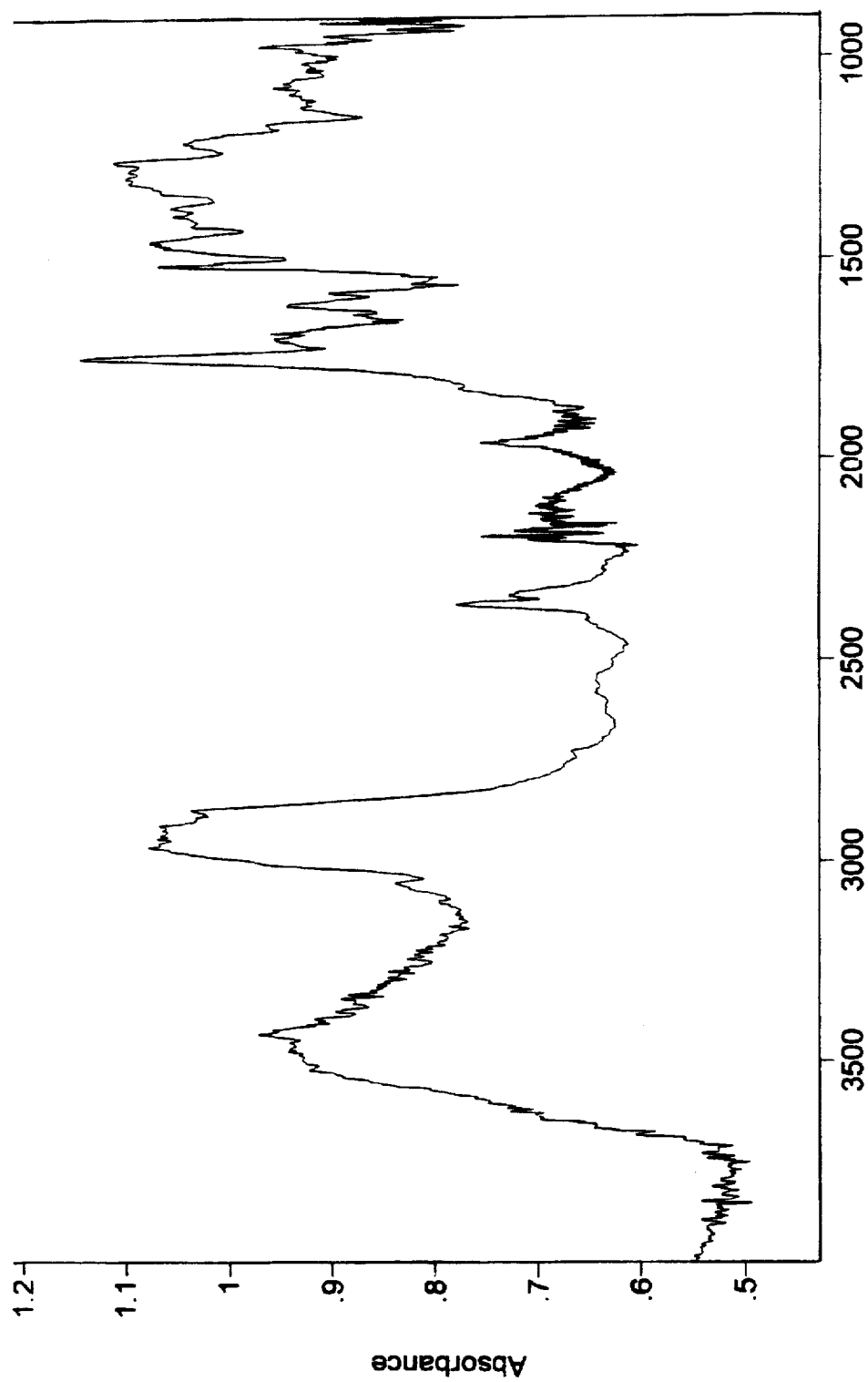
FIG. 6C is an FTIR spectrum of UV-cured epoxy resin on a glass substrate
Figure 6D:
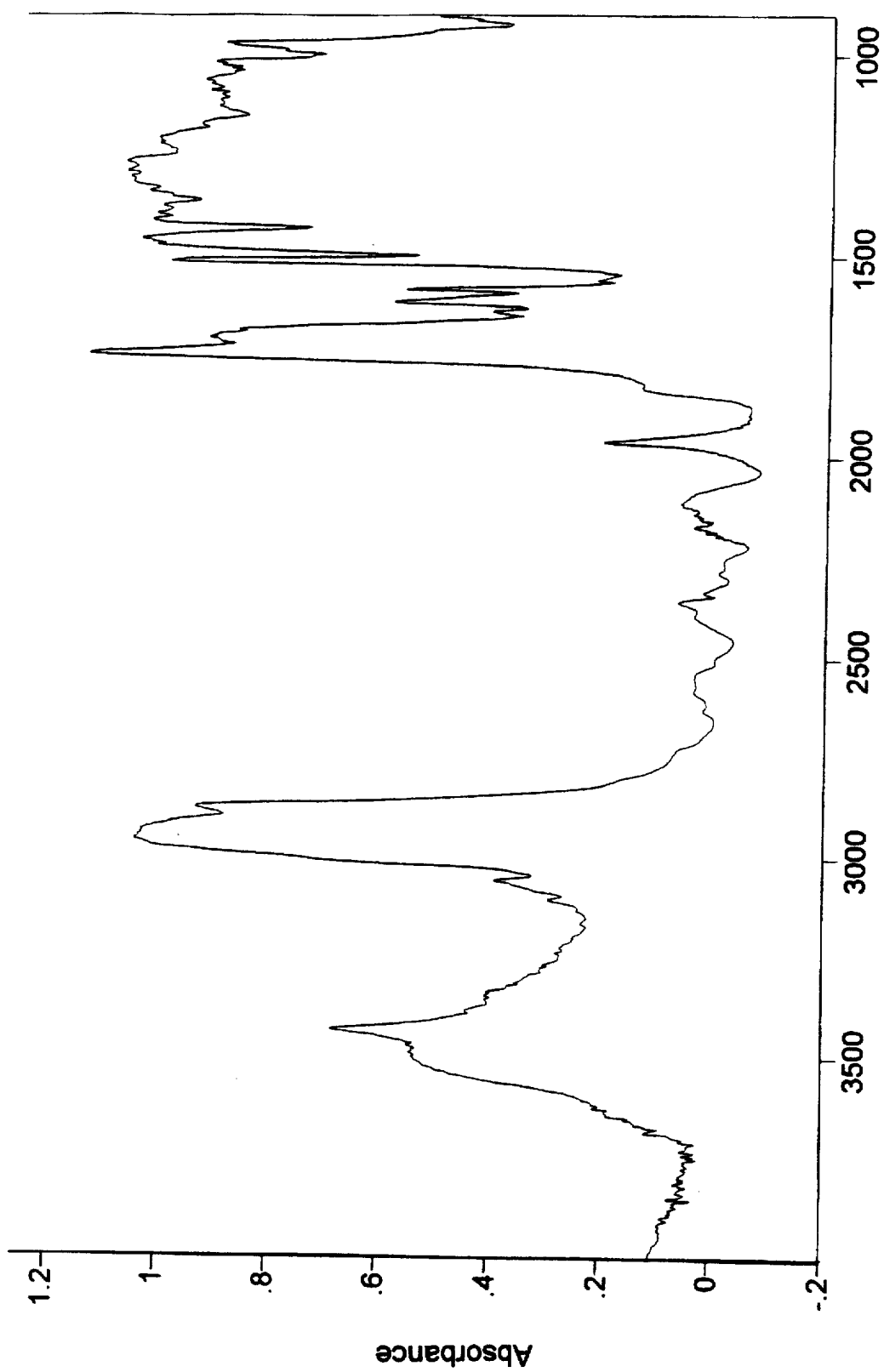
FIG. 6D is an FTIR spectrum of UV-cured epoxy resin on a gold mirror substrate

FIG. 6C shows the reflectance FTIR spectra of a UV-cured epoxy resin. The spectrum was obtained by supporting the cured epoxy resin on a glass substrate, placing the flat end of the reflectance head against the resin surface, and acquiring the spectrum for approx. 2 min.

EXAMPLE 4

Reflectance Head

Spectrum 5C was obtained in the manner described for spectrum 6C, except that the epoxy resin was supported on a gold mirror substrate. In the presence of an almost perfect reflecting surface behind the sample, the IR radiation passes through the epoxy resin (1st pass) and is reflected back through the resin (2nd pass) to the end of the fiber-optic bundle, giving a spectrum that is best described as a double-pass transmission spectrum of the resin.

EXAMPLE 5

Transmission Head

Figure 7A:
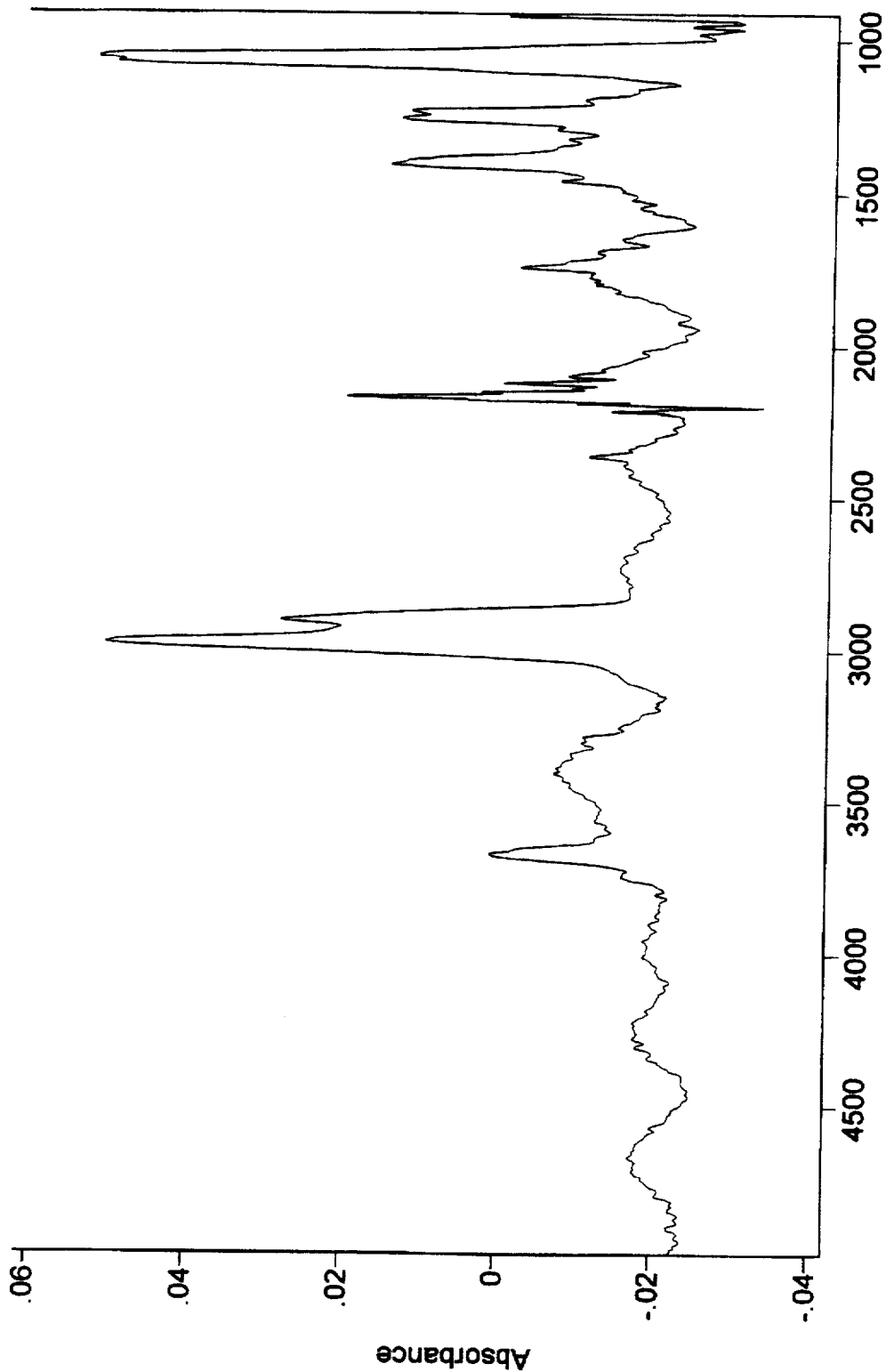
FIG. 7A is an FTIR spectrum of the equilibrium vapor present above the surface of a water-ethanol mixture
Figure 7B:
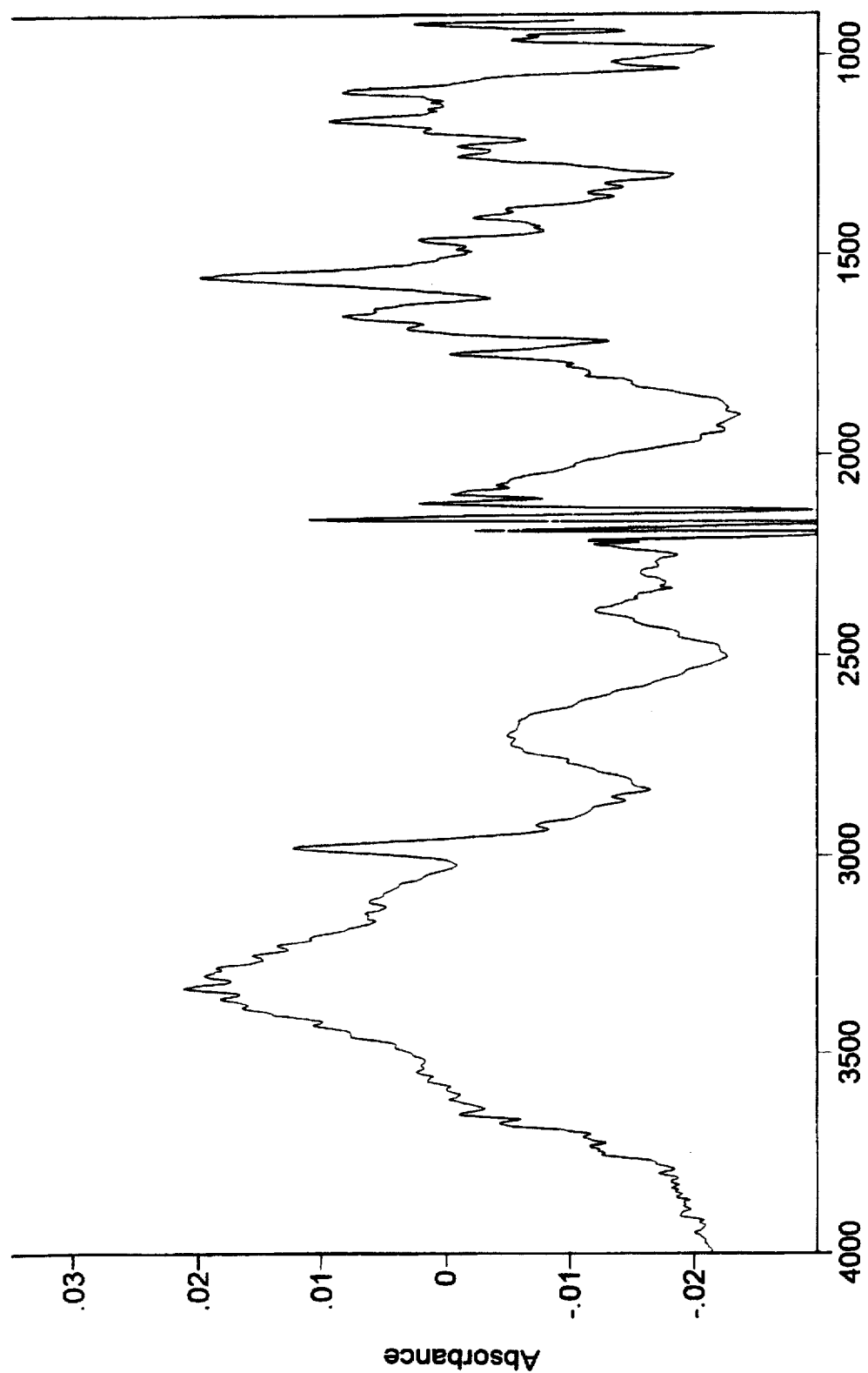
FIG. 7B is an FTIR spectrum of the equilibrium vapor present above the surface of a household cleaner based on aqueous ammonia

FIG. 7A shows the FTIR spectrum of the equilibrium vapor present in the head space of a container of 43 vol. % ethanol in water (in this case, Scotch whisky). The spectrum was obtained by suspending the transmission probe in the head space so that the transmission cell was filled with vapor, then acquiring the spectrum for approx. 2 minutes. The spectrum shown in FIG. 7B was obtained in a similar fashion from the head space in a partially used bottle of ammonia-based household cleaner. The spectrum clearly shows the presence of organic vapors arising from organic components in the cleaner. From the foregoing description and examples, the reader will see that the probe of the invention provides a highly convenient and adaptable way of obtaining spectra from a wide range of different samples in different physical states, merely by changing the screw-fitted head at the end of the probe. In addition, the cost of maintaining separate equipment, and using different procedures, for different types of sample, is eliminated.

While the above description contains many specific details and descriptions, these should not be taken as limiting the scope of the invention, but rather as exemplifications of preferred embodiments. Many other variations are possible, and will be apparent to those skilled in the art. The scope of the invention should be determined not by the embodiments illustrated, but by the appended claims and their legal equivalents.

What is claimed is:

1. A spectroscopic probe for sensing the absorption of infrared energy by a sample, the probe comprising:

(a) a first fiber-optic bundle including a plurality of optical fibers suitable for transmitting the infrared energy from a source of the energy to a sample;

(b) a second fiber-optic bundle including a plurality of optical fibers suitable for transmitting the infrared energy from the sample to a detector;

(c) a shaft within which the optical fibers from the two bundles are combined into one bundle which terminates in a flat end in the end section of the shaft, with the end section of the shaft having mechanical coupling means for directly coupling the end section of the shaft with a sample measuring head which is selected from the set comprising a double-pass transmission cell, an attenuated total reflectance crystal, and a reflectance head, wherein the double-pass transmission cell comprises a hollow extension to the shaft having walls containing a plurality of holes and an end plug having a reflective surface such that the walls of the extension and the surface of the end plug form, together with the end of the fiber-optic bundle, a cell having holes in the side walls to admit a fluid sample so that electromagnetic energy passes from the probe through the sample to the reflecting surface, from which it is reflected back to the fiber-optic bundle, thereby defining a double-pass transmission cell, and wherein the reflectance head comprises a hollow, screw-threaded extension to the shaft of a length which, when its distal end is placed against a sample, enables efficient coupling of infrared energy reflected from the sample into the fiber-optic bundle.

2. A spectroscopic probe according to claim 1 wherein the attenuated total reflectance crystal is coated with a material which selectively interacts with the sample to concentrate the analyte near the surface of the crystal.

3. A spectroscopic probe according to claim 1 wherein the shaft is provided with a cooling jacket and the sample is at an elevated temperature.

4. A spectroscopic probe for sensing the absorption of infrared radiation by a sample, the probe comprising:

(a) a first fiber-optic bundle including a plurality of input optical fibers suitable for transmitting the infrared radiation from a source of the energy to a sample;

(b) a second fiber-optic bundle including a plurality of return optical fibers suitable for transmitting the infrared radiation from the sample to a detector;

(c) a shaft within which the optical fibers from the two bundles are combined into one bundle which terminates in a polished end in the end section of the shaft;

(d) the end section of the shaft having mechanical coupling means for directly coupling the end section of the shaft with a measuring head, and (e) the measuring head comprising a hollow extension to the shaft having walls containing a plurality of holes and an end plug having a reflective surface such that the walls of the extension and the surface of the end plug form, together with the end of the fiber-optic bundle, a cell having holes in the side walls to admit a fluid sample so that electromagnetic energy passes from the probe through the sample to the reflecting surface, from which it is reflected back to the fiber-optic bundle, thereby defining a double-pass transmission cell.

5. A probe according to claim 4 wherein the head contains a protective window which is disposed adjacent the polished end of the fiber-optic bundle in the shaft and with a spacer disposed adjacent the window to determine the length of the cell.

6. A spectroscopic probe according to claim 4 wherein the shaft is provided with a cooling jacket and the sample is at an elevated temperature.

* * * * *